(12) United States Patent
Uzgiris

(10) Patent No.: US 6,235,264 B1
(45) Date of Patent: May 22, 2001

(54) MEDICAL IMAGING METHOD FOR CHARACTERIZING TUMOR ANGIOGENESIS USING POLYMERIC CONTRAST AGENTS

(75) Inventor: Egidijus Edward Uzgiris, Schenectady, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/451,719

(22) Filed: Dec. 1, 1999

(51) Int. Cl.[7] .................................................. A61B 5/055
(52) U.S. Cl. ........................ 424/9.36; 424/9.3; 534/14; 534/15
(58) Field of Search .................................... 424/1.11, 9.1, 424/1.65, 1.37, 1.69, 9.3, 9.34, 9.36; 534/7, 10–16

(56) References Cited

U.S. PATENT DOCUMENTS

| 5,554,748 | * | 9/1996 | Sieving et al. | 540/465 |
| 5,762,909 | | 6/1998 | Uzgiris | 424/9.34 |
| 5,958,372 | * | 9/1999 | Ladd | 424/1.65 |

OTHER PUBLICATIONS

Theodore J. Passe, M.D. et al., Tumor Angiogensis: Tutorial On Implications For Imaging, RSNA, 1997; 203: 593–600.

R. Abramovitch et al., Noevasculariztion Induced Growth Of Implanted c6 Glioma multicellular spheroids: Magnetic Resonance Microimaging, Cancer Research 55, 1956–1962, May 1, 1995.

C. Frouge et al., Correlation Between contrast Enhancement In Dymanic Magnetic Resonance Imaging Of The Breast And TumoSr Angiogensis, Investigative Radiology, vol. 29, Nov. 12, 1994, 1043–1049.

R. Brasch, M.D. et al., Assessing Tumor Angiogensis Using Macromolecular MR Imaging Contrast Media , JMRI Jan./Feb. 1997; 7:68–74.

F. Demsar et al., A MRI Spatial Mapping Technique For Microvascular Permeability And Tissue Blood Volume Based On Macromolecular Constrast Agent Distribution, MRM 37:236–242 (1997).

E.E. Uzgiris, Tumor Uptake Of Constract Agents: The Role Of Molecular Conformation, SMRM Proceedings 1656 (1998).

H.F. Dvork et al., Vascular Permeability Factor/Vascular Endothelial Growth Factor, Microvascular Hyperpermeability, and Angiogenesis, AJP May 1995, vol. 146, No. 5.

F. Scopinaro et al., Technetium–99m Sestamibi: An Indicator Of Breast Cancer Invasiveness, Eur J Nuci Med (1994) 21:987–987.

L.D. Buada, Breast Lesions: Correlation of contrast Medium enhancement Patterns on MR Images With Histopathologic Findings and Tumor Angiogenesis, Radiology, vol. 200, No. 3, pp. 639–349.

N. Weidner, M.D. et al., Tumor Angiogenesis and Metastasis–Correlation In Invasive Breast Carcinoma, The New England Journal Of Medicine, vol. 324: 1–8, 1991.

E. F. Haran et al., Tamoxifen Enchances Cell Death In Implanted MCF7 Breast Cancer By Inhibiting Endothelium Growth, Cancer Research 54, 5511–5514, Nov. 1, 1994.

R.H. Austin et al., Stretch Genes, Physics Today, pp. 32–37, 1997.

PF Sieving et al., Preparation and Characterization of Paramagnetic Polychelates and Their Protein Conjugates, Bioconjugate Chem. 1:65–71, 1990.

D.A. Sipkins et al., Detection of Tumor Angiogenesis in Vivo by AvB3–Targeted Magnetic Resonance Imaging, Nature Medicine, vol. 4, No. 5: 623–626, May 1998.

Pierre–Giles de Gennes, "Entangled Polymers", Physics Today,06/83, pp. 33–39.

Pierre–Giles de Gennes, "Reptation of a Polymer Chain in the Presence of Fixed Obstacles", J. Chem. Physics 55: Jan. 18, 1971, pp. 572–579.

Paul F. Sieving, Alan D. Watson, and Scott M. Rocklage, "Preparation and Characterization of Paramagnetic Polychelates and Their Protein Conjugates", Bioconjugate Chem. vol. 1, Jul. 31, 1989, pp. 65–71.

* cited by examiner

Primary Examiner—Dameron L. Jones
(74) Attorney, Agent, or Firm—Jill M. Breedlove; Douglas E. Stoner

(57) ABSTRACT

In a method for characterizing the angiogenesis status of a tumor in a living subject, timed magnetic resonance images of the subject into whom a reptating polymer contrast agent containing chelating diethylentriaminepentacetic acid dosed with gadolinum has been introduced are obtained. At least two images taken at different times are compared in order to determine the percentage image enhancement in a tumor region of interest.

19 Claims, 2 Drawing Sheets

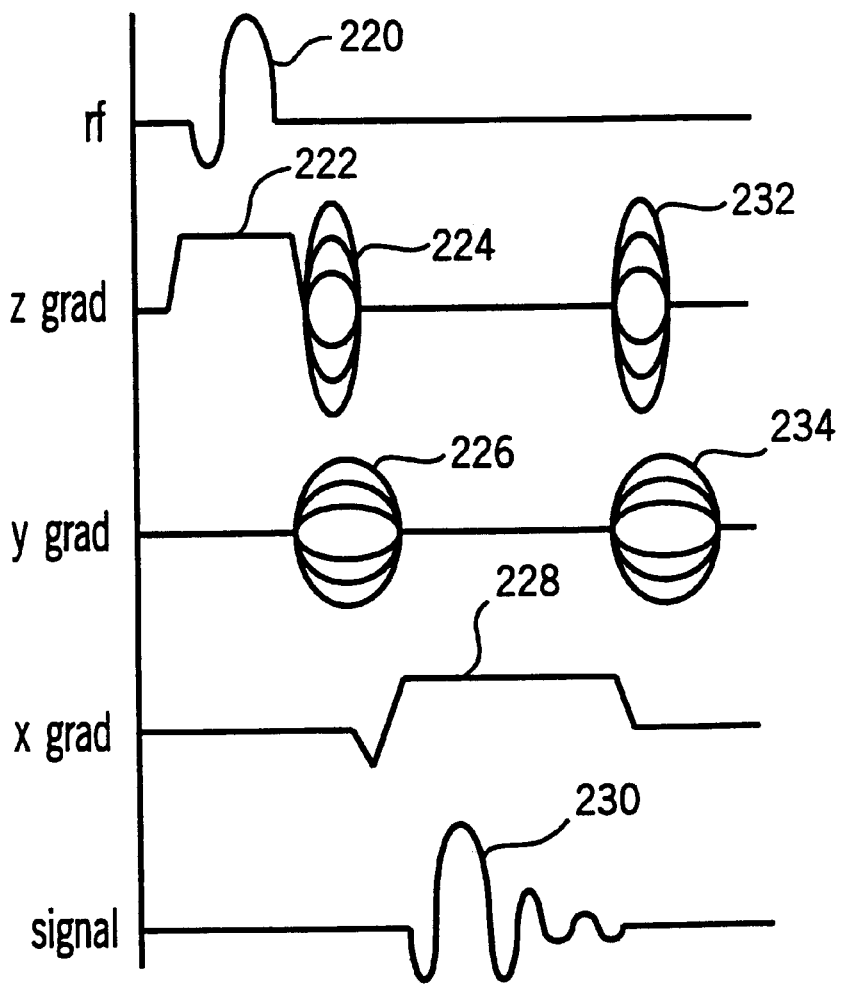

MEDICAL IMAGING METHOD FOR CHARACTERIZING TUMOR ANGIOGENESIS USING POLYMERIC CONTRAST AGENTS

BACKGROUND OF THE INVENTION

This invention relates to nuclear magnetic resonance imaging (MRI) methods and systems and, particularly, to magnetic resonance imaging of tumors using contrast agents.

Tumor angiogenesis is the recruitment of new blood vessels by a growing tumor from existing neighboring vessels. This recruitment of new microvasculature is a central process in tumor growth and in the potential for aggressive spreading of the tumor through metastasis. All solid tumors require angiogenesis for growth and metastasis. Thus, the level of angiogenesis is thought to be an important parameter for the staging of tumors. Furthermore, new therapies are being developed which attack the process of angiogenesis for the purpose of attempting to control tumor growth and tumor spread by restricting or eliminating the tumor blood supply. It is therefore of clinical importance to be able to monitor angiogenesis in tumors in a noninvasive manner.

To assess angiogenic activity of tumors, two parameters are of primary importance: vascular volume and vascular permeability. Invasive techniques utilizing tissue staining can be used to assess microvascular development, but the sensitivity of existing staining methods is not high enough and the prognostic value of such methods is not yet well established (N. Weidner, et al., *New Eng. J. Med.* 324:1–8, 1991). At present there is no single imaging method capable of providing quantitative characterization of tumor angiogenesis.

As for non-invasive methods for assessing the two parameters, there is at present no accepted clinical imaging method for characterizing tumor angiogenesis. (Passe, et al., *Radiology* 203:593–600, 1997). The present invention involves a magnetic resonance imaging method with a type of contrast agent that enables measurement of both vascular volume and vascular permeability with much higher sensitivity than heretofore possible. Such measurement should facilitate independent prognostic assessments of cancer and help in monitoring cancer therapy non-invasively.

When a substance such as living tissue is subjected to a uniform magnetic field (polarizing field $B_0$), individual magnetic moments of the nuclear spins in the tissue attempt to align with this polarizing field along the z axis of a Cartesian coordinate system, but precess about the z axis direction in random order at their characteristic Larmor frequency. If the substance, or tissue, is subjected to a magnetic field (excitation field $B_1$) which is in the x-y plane and at a frequency near the Larmor frequency, the net aligned longitudinal magnetization may be rotated, or "tipped", into the x-y plane to produce a net transverse magnetization. A signal is emitted by the excited spins after the excitation signal $B_1$ is terminated. This NMR signal may be received and processed to form an image.

When utilizing NMR signals of this type to produce images, magnetic field gradients ($G_x$, $G_y$ and $G_z$) are employed. Typically, the region to be imaged is scanned with a series of measurement cycles in which these gradients vary according to the particular localization method being used. The resulting set of received NMR signals is digitized and processed to reconstruct the image using one of many well known reconstruction techniques.

One of the mechanisms employed in MRI to provide contrast in reconstructed images is the $T_1$ relaxation time of the spins. After excitation, a period of time is required for the longitudinal magnetization to fully recover. This period, referred to as the $T_1$ relaxation time, varies in length depending on the particular spin species being imaged. Spin magnetizations with shorter $T_1$ relaxation times appear brighter in MR images acquired using fast, $T_1$ weighted NMR measurement cycles. A number of contrast agents which reduce the $T_1$ relaxation time of neighboring water protons are used as in vivo markers in MR images. The level of signal brightness, i.e., signal enhancement, in $T_1$ weighted images is proportional to the concentration of the agents in the tissue being observed.

In pre-clinical research applications, high-field MRI has been used to assess tumor volume and tumor signal changes in animal models after treatment with tamoxifen, a type of antiangiogenic agent (H. E. Maretzek, et al., *Cancer Res.*, 54:5511–5514, 1994). By using an intravascular contrast agent, albumin-Gd-DTPA, tumor vascular volume and permeability were measured as well as spatial distribution of the neovasculature. In another study using a high polarizing field, tumor growth was followed by using a variety of NMR measurement pulse sequences that allowed the investigators to distinguish microvessels from larger vessels through blood oxygen level dependent effects. Permeability was assessed by noting the time dependent changes in NMR signal when Gd-DTPA was administered to the animal (R. Abramovitch, et al., *Cancer Res.* 55:1956–1962,1995).

At lower polarizing fields that are available at clinical sites, Gd-DTPA, an MRI contrast agent approved by the FDA (U.S. Food and Drug Administration) has been used to estimate angiogenic activity of tumors (C. Frouge, et al., *Invest. Radiol.* 29:1043–1049, 1994). However, this contrast agent is not ideal for characterizing tumor vasculature because it rapidly migrates to the extravascular space before being excreted through the kidneys. The tumor NMR signal measurements become delicate, being based on the dynamics of contrast agent uptake and elimination. Staging of tumors by this approach has been difficult (R. Brasch, et al., *Radiology* 200:639–649,1996).

To avoid the delicate dynamic aspects of Gd-DTPA uptake measurements, others have used a macromolecular contrast agent, albumin—Gd-DTPA (F. Demser, et al., *Mag. Res. Med.* 37:236–242, 1997). In this instance, the elimination process does not play a role in the observed MR signals, so that a much simpler and more reliable signal analysis is possible. Thus, MR signals based on $T_1$ changes (proportional to agent concentration) have provided indications of tumor blood vessel leak rate and tumor blood volume. This then represents an effective imaging method for assessing tumor angiogenesis. There are however, several drawback to this approach. Permeability of tumor vasculature to such macromolecules is not high enough to produce large MR signal changes, thus limiting the sensitivity of this approach. The observable MR signal changes appear to be concentrated mainly at the rim of implanted tumors and a full volume assessment appears to be lacking. However, the most serious obstacle to implementation of this approach is that this macromolecular agent has associated immune reactions when injected and leads to substantial toxicities. Thus, at present, this contrast agent is unsuitable for clinical applications (T. J. Passe, et al., *Radiology* 230:593–600,1997).

BRIEF SUMMARY OF THE INVENTION

In a preferred embodiment of the invention, tumor angiogenesis is characterized by imaging tumors using a reptating polymer contrast agent. The reptating polymer contrast agent is introduced into the subject, and magnetic resonance images of a tumor in the subject are acquired. The initial increase in image enhancement immediately following induction of the contrast agent is a measure of the blood volume and the slow rate of change in image contrast thereafter is a measure of tumor vasculature permeability.

BRIEF DESCRIPTION OF THE DRAWINGS

FIG. 2 is a graphic representation of a pulse sequence performed by the MRI system of FIG. 1 to practice a preferred embodiment of the invention.

DESCRIPTION OF THE PREFERRED EMBODIMENTS

Figure 1:
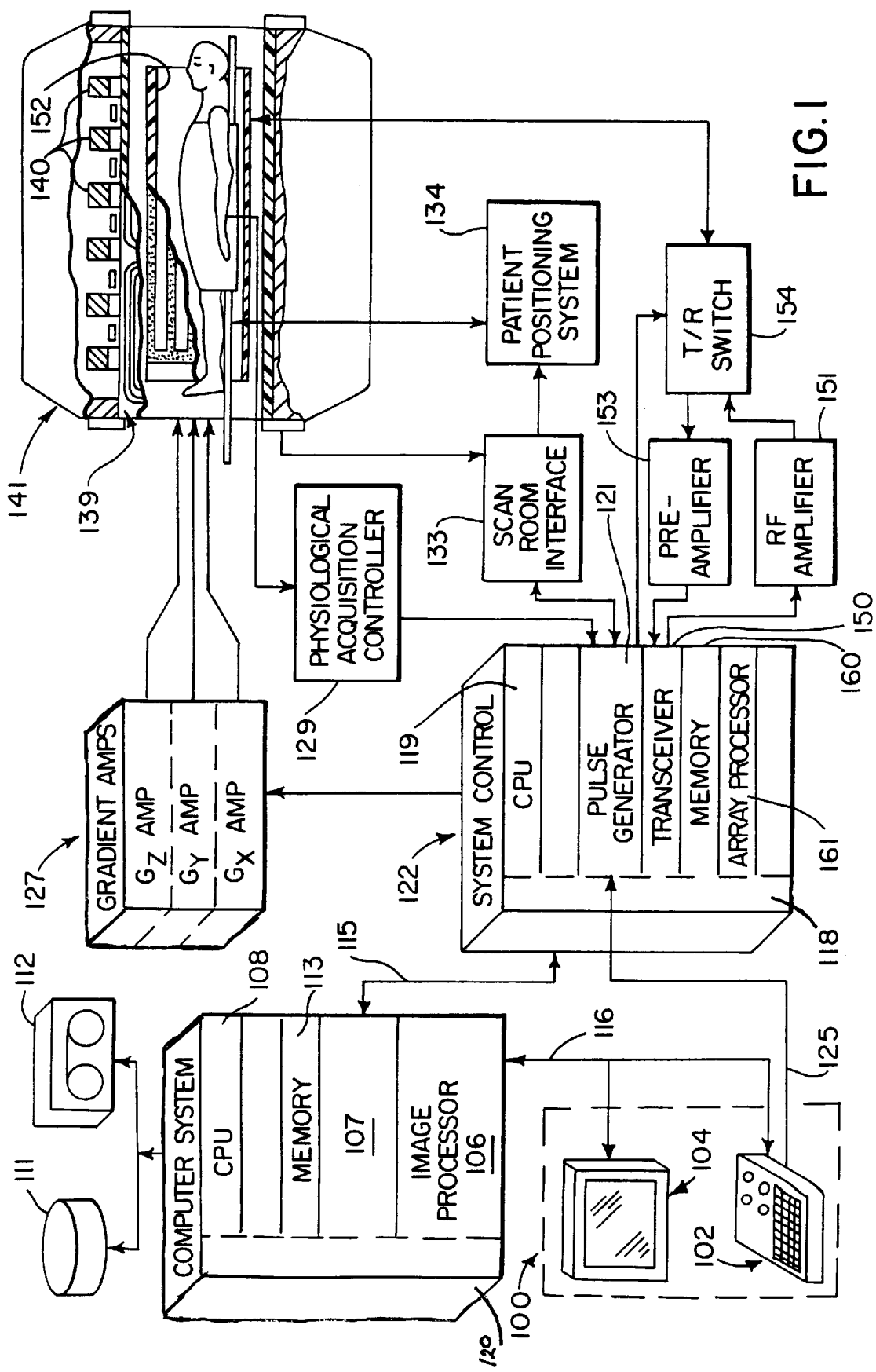
FIG. 1 is a block diagram of an MRI system which employs the present invention.

In a method for characterizing tumor angiogenesis, a contrast agent comprising a reptating polymer is intravenously injected and a series of timed medical images is obtained. A signal enhancement (in $T_1$ weighted images) above a certain threshold, preferably 10%, consititutes an indicator of angiogenic activity. (In the rat tumor model, described below, a signal threshold for angiogenic activity is at least 10% enhancement for an injection dose of 0.025 mmoles Gd/kG.) Signal enhancement will change proportionally to dose of Gd/kG. However, a signal enhancement of at least 10% is preferred. Signals beyond the threshold level will indicate increased angiogenic activity in the form of increased microvascular density, usually at the periphery edges of the tumor, and increased vascular permeability at the periphery and throughout the interior of the tumor.

A preferable contrast agent for practicing the method of the present invention is a reptating polymer, preferably as described in Uzgiris U.S. Pat. No. 5,762,909, issued Jun. 9, 1998 and assigned to the instant assignee. U.S. Pat. No. 5,762,909, incorporated by reference herein, describes the creation of elongated, worm-like macromolecules. A particularly preferred polymer is a homopolymer of lysine where the lysine residues are substituted with Gd-DTPA, or gadolinuim-diethylentriaminepentaaceticacid. The degree of substitution must be very high, in excess of 90%, for the polymer to assume an elongated worm-chain conformation. The polymers described in U.S. Pat. No. 5,762,909 have such a conformation as determined by their measured persistence length (in the range of 100 to 600 Å) which is similar to the persistence length of double-stranded DNA. Double-stranded DNA is a classic reptating polymer and is separated according to length in gel electrophoresis by the mechanism of reptation (R. H. Austin, et al., *Physics Today*, pp. 32–37, 1997). The polymers of U.S. Pat. No. 5,762,909 remain in the vasculature as a blood pool agent and leak out of the endothelium only in tumors which have a hyperpermeable endothelium. The hyperpermeability is a result of angiogenesis signals emanating from tumor cells under nutrient and oxygen stress. The polymers are shown to be ideal agents for MR imaging methods to measure tumor blood volume and tumor endothelium permeability. The polymers for use in a preferred embodiment of the invention are made by substituting the lysine residues of polylysine with DTPA in a mixed anhydride reaction (Sieving, et al. 1:65–71, 1990). However, in order to attain the reptating conformation, the anhydride reaction and the coupling reaction are modified: the synthesis of the anhydride of DTPA is as previously described by Sieving, but the reaction is preferably run between −25° C. and −28° C. for 30 minutes under dry nitrogen atmosphere. The coupling of the anhydride to the lysines is modified in that a much higher molar ratio of anhydride to lysines residues is used in the coupling (from 7 to 10). After the coupling reaction, the reaction solution is subject to roto-vaporation at 50° C. to release all the volatile organic molecules and then the product is purified through extensive dia-filtration (Amicon, 10 kD molecular weight cutoff filters). To achieve the final MR active agent, the paramagnetic ion gadolinium is incorporated into the product polymer chelating DTPA groups by dropwise addition of $GdCl_3$ in 0.1 M HCl (50 mM in Gd) into the polymer solution (15 mM $NaHCO_3$). The dropwise addition of Gd continues until a slight indication of free Gd (not chelated by available DTPA groups) is noted (small aliquots of polymer solution added to 10 $\mu$M of arzenzo IIII in acetate buffer—free Gd turns the dye solution blue). The reptating polymer is then introduced into a blood vessel of the subject.

Other paramagnetic ions besides Gd may be used. However, Gd is the most paramagnetic (i.e., has the most unpaired electrons) and thus is the most effective as contrast agent. A chelator such as DTPA must be used because free Gd is toxic. The chelator folds around the Gd and tightly binds it, but the water protons can come into one Gd coordination site and be relaxed.

A comparable Lanthanide series element that can be used is Dy, dysprosium. All other elements are less effective in relaxing water protons. Iron and manganese (MN(II) and Fe(III) have also been used with much less relaxivity per ion by a factor of about 3 for the DTPA chelate.

The uptake of these molecules, as judged by MR signal enhancements, is more than ten times higher than observed for other macromolecular agents such as compact coiled peptide agents or globular protein, albumin-Gd-DTPA, agents. The extravasation of the polymeric agents in the tumors is thought to be much higher than for the globular agents due to the process of reptation, which allows the polymers to migrate around obstacles in a small convective force field. The globular agents, on the other hand, cannot move through very small pores or around obstacles in a fibrous matrix of the basement membrane of the endothelium and are thus repelled and mostly remain in the blood circulation before being cleared out through the renal or hepatobiliary excretion channels. Hence, globular agents give small tumor signals and small signals of tumor permeability when injected intravenously.

A relatively short chain length polymeric agent (typically about 150–250 monomers or residues) is likely to be most suitable for the present invention. The signal will be reduced from the longer chain of about 500 residues used in these experiments described below by perhaps a factor of 4 for well-known reasons having to do with circulation times and the physics of the reptation process. However, the response of the signal will be faster and the faster blood clearance will be a desirable feature for monitoring and following effects of antiangiogenesis therapy.

Preferred reptating polymers are synthesized either from a homopolymer such as polylysine or from random co-polymers of glutamic acid and lysine. The random co-polymers are more suitable for synthesis of short chain agents and allow for a more robust synthesis procedure.

As mentioned above, one preferred reptating polymer contrast agent is Gd-DTPA-PLL. In one preferred synthesis, polylysine, PLL (degree of polymerization 455, Sigma Aldrich) is substituted with DTPA at very high levels through a modified mixed anhydride method. (P. F. Sieving, et al., *Bioconiugate Chem.* 1:65–71, 1990) Lower levels of substitution are also generated by varying the synthesis conditions appropriately. Highly substituted PLL, containing less than 5% free lysines by the (trinitobenzenesulfonic acid) TNBS (P. Field, *Meth. Enzymol.* 25:464–468, 1972) assay, may be compared with the other constructs for conformational aspects by relaxivity measurements, cryo-electron microscopy, and small angle light scattering. Another preferred synthesis is described in the examples below.

In order to perform one preferred embodiment of the invention, a subject is first imaged and then the contrast agent is introduced into the subject by injecting the contrast agent intravenously at approximately 0.025 mmoles Gd/Kg. The subject is then imaged, preferably beginning immediately after injection and at certain timed intervals. Preferably, the timed intervals are shortly after injection (within 10 minutes) and up to 1 hour post injection. For highest sensitivity of permeability, an image at 24 hours may also be acquired. FIGS. 1 and 2, as described below, illustrate a preferred MRI imaging procedure. To determine changes in blood volume, imaging should take place within 10 minutes of contrast agent injection.

FIG. 1 shows the major components of a preferred MRI system which can be used in practicing the invention. Operation of the system is controlled from an operator console 100 which includes a keyboard and control panel 102 and a display 104. Console 100 communicates through a link 116 with a separate computer system 107 that enables an operator to control the production and display of images on the screen of display 104. Computer system 107 includes a number of modules which communicate with each other through a backplane 120. These include an image processor module 106, a central processing unit (CPU) module 108 and a memory module 113, known in the art as a frame buffer for storing image data arrays. Computer system 107 is linked to a disk storage 111 and a tape drive 112 for storage of image data and programs, and communicates with a separate system control 122 through a high speed serial link 115.

System control 122 includes a set of modules connected together by a backplane 118. These include a CPU module 119 and a pulse generator module 121 which is coupled to operator console 100 through a serial link 125. Through link 125, system control 122 receives commands from the operator which determine the scan sequence that is to be performed.

Pulse generator module 121 operates the system components to carry out the desired scan sequence, and produces data which determine the timing, strength and shape of the RF pulses to be produced, and the timing and length of the data acquisition window. Pulse generator module 121 is coupled to a set of gradient amplifiers 127, to determine the timing and shape of the gradient pulses to be produced during the scan. Pulse generator module 121 also receives patient data from a physiological acquisition controller 129 that receives signals from a number of different sensors attached to the patient, such as electrocardiogram (ECG) signals from electrodes or respiratory signals from a bellows. Pulse generator module 121 is also coupled to a scan room interface circuit 133 which receives signals from various sensors associated with the condition of the patient and the magnet system. Through scan room interface circuit 133, a patient positioning system 134 receives commands to move the patient to the desired position for the scan.

Gradient amplifier system 127 that receives gradient waveforms from pulse generator module 121 is comprised of $G_x$, $G_y$ and $G_z$ amplifiers. Each gradient amplifier excites a corresponding gradient coil in an assembly 139 to produce the magnetic field gradients used for position encoding acquired signals. Gradient coil assembly 139 forms part of a magnet assembly 141 which includes a polarizing magnet 140 and a whole-body RF coil 152. A transceiver module 150 in system control 122 produces pulses which are amplified by an RF amplifier 151 and coupled to RF coil 152 by a transmit/receive switch 154. The resulting signals radiated by the excited nuclei in the patient may be sensed by the same RF coil 152 and coupled through transmit/receive switch 154 to a preamplifier 153. The amplified NMR signals are demodulated, filtered, and digitized in the receiver section of the transceiver 150. Transmit/receive switch 154 is controlled by a signal from pulse generator module 121 to electrically connect RF amplifier 151 to coil 152 during the transmit mode and to connect preamplifier 153 to coil 152 during the receive mode. Transmit/receive switch 154 also enables a separate RF coil (for example, a head coil or surface coil) to be used in either the transmit or receive mode.

The NMR signals picked up by RF coil 152 are digitized by transceiver module 150 and transferred to a memory module 160 in system control 122. When the scan is completed and an entire array of data has been acquired in memory module 160, an array processor 161 operates to Fourier transform the data into an array of image data. These image data are conveyed through serial link 115 to computer system 107 where they are stored in disk storage 111. In response to commands received from operator console 100, these image data may be archived on tape drive 112, or may be further processed by image processor 106 and conveyed to operator console 100 for presentation on display 104.

Although the invention can be used with a number of different pulse sequences, a preferred embodiment of the invention employs a fast 3D (three dimensional) RF (radio frequency) phase spoiled gradient recalled echo pulse sequence, depicted in FIG. 2, to acquire the NMR image data. The pulse sequence "3dfgre" available on the General Electric 1.5 Tesla MR scanner sold by General Electric Company, Milwaukee, Wis., under the trademark "SIGNA" with revision level 5.5 system software is used.

As shown in FIG. 2, an RF excitation pulse 220 having a flip angle of from 40° to 60° is produced in the presence of a slab select gradient pulse 222 to produce transverse magnetization in the three-dimensional (3D) volume of interest as taught in Edelstein et al. U.S. Pat. No. 4,431,968, issued Feb. 14, 1984 and assigned to the instant assignee. This is followed by a slice encoding gradient pulse 224 directed along the z axis and a phase encoding gradient pulse 226 directed along the y axis. A readout gradient pulse 228 directed along the x axis follows, and a partial echo (60%) NMR signal 230 is acquired and digitized as described above. After the acquisition, rewinder gradient pulses 232 and 234 rephase the magnetization before the pulse sequence is repeated as taught in Glover et al. U.S. Pat. No. 4,665,365, issued May 12, 1987 and assigned to the instant assignee. As is well known in the art, the pulse sequence is repeated and the respective slice and phase encoding gradient pulses 224 and 226 are stepped through a series of values to sample the 3D k-space.

The acquired 3D k-space data set is Fourier transformed along all three axes and a magnitude image is produced in which the brightness of each image pixel indicates the NMR signal strength from each corresponding voxel in the 3D volume of interest.

An initial signal is then compared with the signal enhancement observed at selected times, preferably a short time after injection (within 10 minutes) and then at several time points up to 60 minutes post injection. For highest sensitivity to measure endothelial permeability of the tumor, a subsequent image at about 24 hours may also be taken. The initial image after injection (within 10 minutes) provides a measure of tumor blood volume or microvascular density, for each pixel of the image. Subsequent images then establish the rate of leakage into the tumor interstitium, again on a pixel by pixel basis. Maps of blood volume and of endothelium permeability may then be generated and displayed as an image or overlaid on the MR image directly. Both anatomical and physiological features will then be displayed simultaneously, giving radiologists not only the level of angiogenesis as an average quantity but also its activity as a function of position—a very desirable feature for staging and prognosis.

Signal enhancements at the endpoint of about 24 hours, that are below some threshold value, preferably about 10% (for the canonical dose of 0.025 mmoles Gd/Kg), signify minimal angiogenesis activity, as the examples given below imply. Higher signal values (preferably 75%, most preferably 90%) imply ever increasing angiogenic activity. The endpoint signals at 24 hours are due to capillary leakage, as blood concentration levels at that time will be negligibly small for the contrast agents described here, i.e., the reptating polymer agents (although this would not be the case for globular protein agents whose blood circulation time constant may be 24 hours and longer). In growing tumors, the endpoint signals may be expected to be as high as 200% in peripheral regions where neovasculature development is at its highest during angiogenesis.

The reptating polymer contrast agent confers a number of advantages over previous methods that involved the use of small extracellular agents or large macromolecular agents.

First, the polymeric agent does not leave the tumor at an appreciable rate over many hours, thus simplifying the uptake dynamics upon which the assay for angiogenesis is based.

Second, the signal changes observed with the reptating polymer agent are approximately 10 times higher than observed with an albumin agent or with the extracellular agent Gd-DTPA. Thus, this restating polymer contrast agent provides a much higher sensitivity to changes in tumor permeability and yields significant changes in signal over the entire tumor volume unlike what is observed for the albumin agents.

Third, vascular permeability probed with a reptating polymer may be qualitatively different from that probed with a large globular protein such as albumin: the endothelial layer structures that result in the observed leakage in these two instances may be different. In the latter instance, a fragmentation of the basement membrane is required as well as existence of loose endothelial cell junctions for the albumin to be transported out of the vasculature. For reptating polymers, the junctions may be tighter, the basement membrane may not need to be as fragmented, or there may be specific transport mechanisms involving transendothelial transport. For example, in the tumor stroma, considerable levels of fibrinogen are found. This plasma protein has a long, extended conformation and high negative charge. The accumulation of fibrinogen in tumors appears to be associated with angiogenesis and is necessary for conversion of the extracellular matrix into a form conducive to cell growth. Thus, the uptake of the reptating polymer (which is also of high negative charge and is extended in form) may mimic the natural transport processes associated with angiogenesis much more closely than will the uptake of globular proteins.

Fourth, as observed by MRI signal changes, there appears to be little accumulation of the polymeric agent in organs such as liver, kidney or muscle. The clearance of the agent from these organs appears to follow the blood circulation decay rate and no trapping or prolonged binding is evident in these tissues. Furthermore, the blood circulation times can be adjusted by varying the polymer length. For short polymers (of 140–150 residues) the circulation time constant can be as short as 15 minutes (equal to the circulation time of the extracellular agent, Gd-DTPA). Thus, at present, there are no indications that toxicity will become an issue with these types of agents.

In addition to MRI, it is also possible to use nuclear imaging techniques with the polymeric agents. Presently the Gd is chelated in the DTPA polymer chain. It is possible to incorporate, for example, technetium-99 as well as the Gd in such a polymer. The agent uptake will still occur by the reptation mechanism. However, the imaging would be made in this instance through nuclear gamma radiation detection. This can be an alternative to the technetium-99 technique for angiogenesis evaluation with the advantages of a higher uptake of the reptating polymer agent.

EXAMPLES

An animal model was used to demonstrate the MR imaging effects associated with angiogenesis. Fisher female rats were implanted subcutaneously with rat mammary adenocarcinoma cells (ATTC Mat B cells) that were grown to a suitable density in tissue culture. The implanted cells grew into tumors of 1–2 cm diameter in about 10 to 14 days and continued to grow to larger sizes when experiments extended beyond that time frame. Small fragments of tumor were then excised and subcutaneously implanted into a recipient animal as part of an ongoing experimental protocol.

Occasionally, after a number of such passages, the tumor in a recipient animal grew very slowly to a small size (<5 mm in diameter) and ceased to grow any further (over a further period of 7–10 days). Such tumors were models for what is assumed to be a failed ability to elicit angiogenesis to enable further tumor growth. It was observed first by Folkman (J. Folkman, *New Eng. J. Med.* 285:1182–1186, 1971) that tumors failing to grow beyond a certain small size lacked the capacity to recruit a new microvasculature and that this limited their growth. Thus, this class of small, static tumors in this rat model are considered to be deficient in angiogenesis.

The other class of tumors in this animal model comprises tumors that grew larger than 1 cm in a 10–14 day period and continued to grow beyond that time.

The reptating polymer that was used (Gd-DTPA-PLL) was synthesized using a synthesis method described above with 90% of lysines acylated with DTPA and of mean chain length of 613 monomers. The animals were injected intravenously at a dose of 0.025 mmoles Gd/kG. The imaging was done 24 hours after injection with a $T_1$ weighted spin echo pulse sequence (TR=250 ms, TE=18 ms).

Signals from both kinds of tumors, growing tumors and small static tumors, were compared after injecting with reptating polymers and imaging after a fixed period of time (24 hours). Also compared were dynamic signals obtained from both kinds of tumors with Gd-DTPA. This comparison was done as an additional way to confirm that the tumor vasculature permeability was different in the two tumor types. The results are summarized in Table 1 below.

As discussed above and shown in Table 1, there were rapid dynamic changes in tumor signal for both kinds of tumors with the extracellular agent, Gd-DTPA. In the growing tumors, the various regions of interest in the tumor showed exponentially decreasing levels of MR signal with a time constant that was very much slower than observed for muscle or liver. The slower clearance rate is a signature of Gd-DTPA entry into the tumor (and restricted clearance from that volume). In the small, static tumor, the extracellular agent was cleared at the same rate as from muscle or liver tissue, indicating reduced entry from the vascular space into the tumor stroma.

The results with the reptating polymer were striking. For the growing tumors, the enhancement in the peripheral region of the tumors was 200% after 24 hours (for 0.025 mmole Gd/kG dose), whereas for the small static tumors the enhancement for equivalent dose was less than 5%, the experimental error. Thus, a large dynamic range of signal is available with the polymeric agents to assess tumor angiogenesis. Blood volume could be assessed by noting tumor enhancement shortly after intravenous injection (within 10 minutes). Again, in the periphery of tumor, where angiogenic activity is thought to be highest, the immediate enhancement was the highest, ranging from 45% to 10% for 0.025 mmole Gd/kG. An image map of this enhancement will thus be a map of the microvascular development in the tumor.

The permeability of a particular region is proportional to the rate of change of signal after the initial "step" signal rise following injection of the agent. In the absence of loss terms from the tumor volume, the signal after a fixed time post injection is also proportional to the leak rate of the tumor endothelium. The signal change after a fixed time was shown to be quite different for the two types of tumors. The restricted porosity of the small static tumors that this observation implied was corroborated with the dynamic Gd-DTPA measurements. The fast observed clearance of Gd-DTPA from the small, static tumors indicated a limited entry into the tumor stroma. Yet, the initial tumor enhancement levels after Gd-DTPA injection were similar, corroborating what is well known in breast cancer: benign tumors cannot be distinguished from malignant tumors by Gd-DTPA signal enhancement levels.

Thus, with a reptating polymer, the tumor signal enhancement levels are much higher than seen with albumin-Gd-DTPA or with the clinical contrast agent Gd-DTPA. (When normalized to dose, the signals observed with the reptating polymer are 10 times higher). The sensitivity to changes in angiogenesis development will therefore be much higher. Because the polymer is cleared from the tumor only very slowly, measurement of blood volume and endothelium permeability, the two key parameters of angiogenesis, can be performed simply and with high accuracy owing to the strong signals achieved with this agent. The vascular density can be deduced from the initial signal levels after intravenous injection and the permeability can be deduced by the rate of change of signal over time or at a terminal measurement after some 24 hours for example. These signal changes can be displayed as an image map, which will quantitatively display the heterogeneity of angiogenesis development. It is known that tumors are often heterogeneous in vascular development (L. D. Baudu et al, *Radiology* 200:639–649, 1996) and this feature may be important to display and may have prognostic value.

The measurement of the two key parameters of angiogenesis cannot be easily accomplished with the clinical MR contrast agent, Gd-DTPA. Because of its rapid intravascular-extravascular exchange, the permeability measurements are not very sensitive (R. Brasch, et al., *JMRI* 7:68–74, 1997).

Also for the same reason, the blood volume measurements are subject to some error and require good control of the timing of injection. Even so, the variable loss of Gd-DTPA from the vasculature in the first pass of the bolus through the tumor, (Brasch, et al., supra, 1997) may produce errors in the deduced blood volume. These effects make dynamic MR imaging with Gd-DTPA challenging and may in part be the reason for incomplete resolution of benign from cancerous lesions in the breast.

In principle, globular protein agents such as Gd-DTPA-albumin work in this application as discussed above, even if in practice the albumin agent cannot be used in clinical examination because of toxicity. However, the globular agents will not have high sensitivity for permeability because of the very slow leak rates associated with large globular molecules (D. A. Kovar, et al., *Proceedings of ISMRM*, p. 1652, 1998). Fundamentally, the large globular molecules probe permeability associated with large pore structures, whereas reptating molecules can also probe the permeability of smaller pore structures also. The latter may be far more prevalent and important in the neovasculature of tumors.

A further comparison is useful. Sipkins, et al. (D. A. Sipkins, et al., *Nature Medicine* 4:623–626, 1998) have attempted to explicitly label the endothelium of tumors when angiogenesis is active by using an antibody raised against a membrane protein of tumor endothelium cells. The antibody was linked to polymerized liposomes with many Gd-DTPA groups on the surface. The antibody directed liposomes did indeed light up large tumors grown in rabbits after intravenous injection and imaging 24 hours later. However, when normalized by dose of Gd, the MR signal enhancement was 3 times less than observed with the reptating polymers. The approach embodied in this invention is more effective in delineating tumor angiogenic active regions than even specifically directed agents. The reason for the lower specific signals is that the density of antigen sites is not very high. Thus, even when carriers of contrast with a large number of Gd ions are used with the specific antibodies, the levels of MR signals are somewhat limited (R. Lauffer, *Chem. Rev.* 87:901–927, 1987).

TABLE 1

Tumor enhancement signals with reptating polymer agent and Gd-DTPA signal lifetimes in tissues and for growing tumors vs. small static tumors.

| Tissue type | Signal enhancement with polymer | Gd-DPTA signal lifetime, minutes |
| --- | --- | --- |
| tumor, static, small | <5 | 22 |
| tumor, growing | 200 | 45 |
| muscle | — | 18 |
| liver | — | 15 |

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A method for determining the angiogenesis status of a tumor comprising the steps of:

a) obtaining at least two magnetic resonance images of a target tumor region in a subject in which a reptating polymer contrast agent containing chelating diethylentriaminepentaacetic acid (DTPA) dosed with gadolinium (Gd) has been introduced into the subject prior to obtaining at least one image; and b) comparing the images in order to determine a percentage of image enhancement in the tumor region, whereby an image enhancement of at least 10% is indicative of a tumor with an angiogenesis status suggestive of a growing tumor.

2. The method of claim 1 wherein elapsed time between acquisition of the images is 10 minutes or less for the purpose of determining changes in blood volume.

3. The method of claim 1 wherein the reptating polymer contrast agent comprises a homopolymer of lysine wherein the lysine residues are substituted with Gd-DTPA.

4. The method of claim 1, wherein the reptating polymer contrast agent comprises polysine substituted with DTPA.

5. The method of claim 1 wherein the dose of Gd is 0.025 mmole Gd/KG.

6. A method for determining the angiogenesis status of a tumor comprising the steps of:

a) obtaining at least two magnetic resonance images of a target tumor region in a subject in which a reptating polymer contrast agent containing chelating diethylentriaminepentaacetic acid (DTPA) dosed with gadolinium (Gd) has been introduced into the subject after obtaining the first image and prior to obtaining the second image; and b) comparing the images in order to determine a percentage of image enhancement in the tumor region, whereby an image enhancement of at least 10% indicates a tumor with an angiogenesis status suggestive of a growing tumor.

7. The method of claim 5 wherein elapsed time between introduction of the reptating polymer contrast agent into the subject and acquisition of the first image is up to one hour and elapsed time between said introduction and acquisition of the second image is up to 24 hours.

8. The method of claim 6 wherein the reptating polymer contrast agent comprises a homopolymer of lysine wherein the lysine residues are substituted with Gd-DTPA.

9. The method of claim 6 wherein the reptating polymer contrast agent comprises polysine substituted with DTPA.

10. The method of claim 6 wherein the dose of Gd is 0.025 mmole Gd/KG.

11. The method of claim 1 wherein the reptating polymer contrast agent is doped with dysprosium.

12. A method for determining the angiogenesis status of a tumor comprising the steps of:

a) producing a polarizing magnetic field in a subject;

b) performing a series of pulse sequences with an MRI system to acquire a corresponding series of NMR signals, each of said pulse sequences including:
  i) generating an RF excitation pulse to produce transverse magnetization in a tumor region of interest in the subject;
  ii) producing a magnetic field gradient pulse; and
  iii) acquiring, in the presence of a magnetic field gradient produced by said magnetic field gradient pulse an NMR signal produced by the transverse magnetization;

c) reconstructing a first image from the acquired NMR signals; and d) introducing a reptating polymer contrast agent containing chelating diethylentriaminepentaacetic acid (DTPA) dosed with gadolinium (Gd) into the subject and repeating steps a)–c) at least one time to reconstruct a second image; and e) comparing the first and second images in order to determine a percent image enhancement in the tumor region of interest, whereby an image enhancement of at least 10% is indicative of a tumor with an angiogenesis status suggestive of a growing tumor.

13. The method of claim 12 wherein time elapsed between acquisition of the images is 10 minutes or less for the purpose of determining changes in blood volume.

14. The method as recited in claim 12 in which the magnetic field gradient pulse is shaped to produce a gradient recalled NMR echo signal for use in reconstructing the first image.

15. The method as recited in claim 12 including the step of producing a second magnetic field gradient pulse in each of the pulse sequences, wherein the tumor region of interest in the subject is a two-dimensional slice.

16. The method as recited in claim 15 including the step of producing a third magnetic field gradient pulse in each of the pulse sequences, wherein the tumor region of interest in the subject is a three-dimensional volume.

17. The method as recited in claim 12 wherein step c) includes performing a Fourier transformation on the NMR signals.

18. The method of claim 12 wherein the second image of step d) is acquired at about 24 hours after the step of introducing the reptating polymer contrast agent into the subject.

19. The method of claim 12 wherein the reptating polymer contrast agent comprises a homopolymer of lysine wherein lysine residues are substituted with Gd-DTPA.

* * * * *